US012622847B2

(12) United States Patent
Murayama et al.

(10) Patent No.: US 12,622,847 B2
(45) Date of Patent: May 12, 2026

(54) ORGANOSILICON COMPOUND AND DENTAL COMPOSITION CONTAINING SAME

(71) Applicant: Kuraray Noritake Dental Inc., Kurashiki (JP)

(72) Inventors: Ryota Murayama, Niigata (JP); Ryo Matsuura, Niigata (JP); Yamato Nojiri, Tokyo (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 544 days.

(21) Appl. No.: 18/269,347

(22) PCT Filed: Dec. 24, 2021

(86) PCT No.: PCT/JP2021/048429

§ 371 (c)(1),
(2) Date: Jun. 23, 2023

(87) PCT Pub. No.: WO2022/138974

PCT Pub. Date: Jun. 30, 2022

(65) Prior Publication Data

US 2024/0164993 A1 May 23, 2024

(30) Foreign Application Priority Data

Dec. 25, 2020 (JP) ................................ 2020-218057

(51) Int. Cl.
*A61K 6/30* (2020.01)

(52) U.S. Cl.
CPC ...................................... *A61K 6/30* (2020.01)

(58) Field of Classification Search
CPC ........................................................ A61K 6/30
USPC ........................................................ 523/118
See application file for complete search history.

(56) References Cited

U.S. PATENT DOCUMENTS

| | | | | |
|---|---|---|---|---|
| 4,221,698 | A | 9/1980 | Lee, Jr. et al. | |
| 4,719,297 | A | 1/1988 | Henne et al. | |
| 5,017,668 | A | 5/1991 | Yoshihoka et al. | |
| 11,607,370 | B2 * | 3/2023 | Matsuura | A61K 6/838 |
| 2010/0069524 | A1 | 3/2010 | Tanaka et al. | |
| 2021/0186823 | A1 * | 6/2021 | Matsuura | A61K 6/30 |
| 2022/0142874 | A1 * | 5/2022 | Kajikawa | A61K 6/76 |

FOREIGN PATENT DOCUMENTS

| | | | | |
|---|---|---|---|---|
| EP | 0009348 B1 | | 4/1980 | |
| EP | 0508491 A1 | | 10/1992 | |
| EP | 2840431 A1 | | 2/2015 | |
| JP | S57-197289 A | | 12/1982 | |
| JP | H01-292018 A | | 11/1989 | |
| JP | H02-133338 A | | 5/1990 | |
| JP | H05202071 A | | 8/1993 | |
| JP | 2008001624 A | | 1/2008 | |
| JP | 2008137918 A | | 6/2008 | |
| JP | 2013222141 A | | 10/2013 | |
| JP | 2017049327 A | | 3/2017 | |
| JP | 2019099472 A | | 6/2019 | |
| WO | WO-2008053990 A1 | | 5/2008 | |
| WO | WO-2019082855 A1 | * | 5/2019 | A61K 6/887 |
| WO | WO-2020122192 A1 | * | 6/2020 | A61K 6/889 |

OTHER PUBLICATIONS

Extended European Search Report issued Jun. 17, 2025, in corresponding European Patent Application No. 21911111.9, 11 pages.
International Search Report issued Mar. 1, 2022 in PCT/JP2021/048429 (with English translation), 4 pages.
Written Opinion issued Mar. 1, 2022 in PCT/JP2021/048429 (with English translation), 6 pages.

* cited by examiner

*Primary Examiner* — Deve V Hall
(74) *Attorney, Agent, or Firm* — Element IP, PLC

(57) ABSTRACT

The present invention provides a dental composition that shows improved adhesive properties to dental restoration materials such as porcelain, as well as tooth structure, and that is suited for reducing property changes during storage. The present invention relates to a dental composition comprising an organosilicon compound (A) represented by the following general formula (1), $$Z—X_m—Y—SiR^1_nR^2_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$, $R^2$, and X each may be the same or different when $R^1$, $R^2$, or X is plural.

18 Claims, No Drawings

ORGANOSILICON COMPOUND AND DENTAL COMPOSITION CONTAINING SAME

TECHNICAL FIELD

The present invention relates to a novel organosilicon compound, and a dental composition containing same.

BACKGROUND ART

In response to the recent demand for dental restorations that not only offer functionality but also enhance aesthetics post-restoration, ceramic materials such as composite resins, zirconia, alumina, lithium disilicate glass, and porcelain have come to be used as dental restoration materials for crown restorations, alongside traditional metals. Dental primers and dental adhesives are used to bond such dental restoration materials to an adherend.

Examples of dental primers and dental adhesives are disclosed. For example, Patent Literature 1 discloses a specific one-pack type dental primer comprising a silane coupling agent, an acidic group-containing polymerizable monomer, and a volatile organic solvent. Patent Literature 2 discloses a one-pack type adhesive composition that comprises a specific silane coupling agent, an acidic group-containing polymerizable monomer, a primary alcohol, and water, and in which the water content is 0.005 to 0.5 mass %.

Over the years, there has been an increase in the versatility of dental compositions, and there is a growing need for a one-pack type dental composition that can be used as a single component on many adherends, including the tooth structure. However, because dental restoration materials such as porcelain greatly differ in material properties from tooth structure, it has been difficult to impart high adhesive properties to both of these materials. In view of such adhesive properties, the compositions described in Patent Literatures 1 and 2 need further improvements. Adding water is one possible method of improving adhesive properties to tooth structure. However, simply adding water results in a serious reduction in the preservation stability of a silane coupling agent, and decreases the adhesive properties to dental restoration materials.

As a technique to overcome the foregoing issues, an example of a one-pack type dental composition that can be applied as a single component to a wide range of adherends, including both dental restoration materials and tooth structure, can be found in Patent Literature 3, which discloses a dental composition that comprises a specific silane coupling agent, an acidic group-containing polymerizable monomer, and water, and in which the water content is 1.0 to 50 mass %.

CITATION LIST

Patent Literature

Patent Literature 1: WO2008/053990
Patent Literature 2: JP 2008-1624 A
Patent Literature 3: WO2019/082855

SUMMARY OF INVENTION

Technical Problem

However, studies by the present inventors revealed that, aside from adhesive properties, the dental composition described in Patent Literature 3 undergoes a viscosity increase or shows a high degree of thixotropy during long storage, though the dental composition exhibits high adhesive properties to dental restoration materials such as porcelain, as well as tooth structure, as stated. Additionally, it was newly found that further improvements are needed in terms of ease of handling because the level of ease of handling immediately after production cannot last over an extended time period of long storage, making it difficult to dispense the dental composition from its container, or apply the dental composition in a layer over a surface of an adherend. That is, there is still room for improvement in terms of property stability during storage.

It is accordingly an object of the present invention to provide a dental composition that shows improved adhesive properties to dental restoration materials such as porcelain, as well as tooth structure, and that is suited for reducing property changes during storage.

Solution to Problem

The present inventors conducted intensive studies to provide a solution to the foregoing issues, and found that a dental composition comprising an organosilicon compound having a specific structure shows improved adhesive properties to dental restoration materials such as porcelain, as well as tooth structure, and is suited for reducing property changes during storage. The present invention was completed after further studies based on this finding.

Specifically, the present invention includes the following.

[1] A dental composition comprising an organosilicon compound (A) represented by the following general formula (1), $$Z—X_m—Y—SiR^1_nR^2_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$, $R^2$, and X each may be the same or different when $R^1$, $R^2$, or X is plural.

[2] The dental composition according to [1], wherein the number of carbon atoms in X is 1 to 3.

[3] The dental composition according to [1] or [2], wherein X is a group represented by the following formula (2), (3), or (4), $$—CH_2O— \quad (2)$$

$$—CH_2CH_2O— \quad (3)$$

$$—CH_2CH_2CH_2O— \quad (4).$$

[4] The dental composition according to any one of [1] to [3], wherein m is an integer of 1 to 4.

[5] The dental composition according to any one of [1] to [4], wherein n is 1 or 2.

[6] The dental composition according to any one of [1] to [5], wherein Z is a (meth)acryloyloxy group.

[7] The dental composition according to any one of [1] to [6], wherein $R^2$ is an alkoxy group having 1 to 5 carbon atoms.

[8] The dental composition according to any one of [1] to [7], wherein the content of the organosilicon compound (A) is 0.1 to 50 mass %.

[9] The dental composition according to any one of [1] to [8], which further comprises a monomer (B) having an acidic group.

[10] The dental composition according to [9], wherein the monomer (B) having an acidic group comprises a monomer having a phosphoric acid group.

[11] The dental composition according to any one of [1] to [10], which further comprises water (C).

[12] The dental composition according to any one of [1] to [11], which further comprises a monomer (D) having no acidic group.

[13] The dental composition according to [12], wherein the monomer (D) having no acidic group comprises a hydrophilic monomer (D-2) having no acidic group.

[14] The dental composition according to [13], which comprises 8 to 90 mass % of the hydrophilic monomer (D-2) having no acidic group based on the mass of all monomers contained in the dental composition.

[15] A dental adhesive comprising a dental composition of any one of [1] to [14].

[16] An organosilicon compound (A) represented by the following general formula (1), $$Z—X_m—Y—SiR^1{}_nR^2{}_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$, $R^2$, and X each may be the same or different when $R^1$, $R^2$, or X is plural.

[17] The organosilicon compound (A) according to [16], wherein the number of carbon atoms in X is 1 to 3.

[18] The organosilicon compound (A) according to [16] or [17], wherein X is a group represented by the following formula (2), (3), or (4), $$—CH_2O— \quad (2)$$

$$—CH_2CH_2O— \quad (3)$$

$$—CH_2CH_2CH_2O— \quad (4).$$

Advantageous Effects of Invention

According to the present invention, a dental composition can be provided that shows improved adhesive properties to dental restoration materials such as porcelain, as well as tooth structure, and that is suited for reducing property changes during storage. The present invention can also provide a dental composition that excels in preservation stability by showing improved adhesive properties to dental restoration materials such as porcelain, as well as tooth structure, even after long storage. A dental composition provided by the present invention also excels in ease of handling because it can sustain the level of ease of handling immediately after production over an extended time period of long storage, and can be easily dispensed from its container, even when stored for an extended time period by being filled into a container.

DESCRIPTION OF EMBODIMENTS

The present invention is described below in detail. In the present specification, the upper limits and lower limits of numeric ranges (for example, ranges of contents of components, ranges of values calculated from components, and ranges of physical properties) can be appropriately combined.

A dental composition of the present invention is a dental composition comprising an organosilicon compound (A) represented by the following general formula (1), $$Z—X_m—Y—SiR^1{}_nR^2{}_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$ and $R^2$ each may be the same or different when $R^1$ or $R^2$ is plural, and X may be the same or different when X is plural.

By containing an organosilicon compound (A) represented by general formula (1), a dental composition of the present invention shows high adhesive properties to dental restoration materials such as porcelain, as well as tooth structure, and undergoes small property changes during storage.

It remains somewhat unclear why the present invention can produce such outstanding effects with such a configuration. However, the following speculations have been made. The spacers of silane coupling agents that have been used for dental applications in the past are almost entirely alkyl groups, and provide relatively high hydrophobicity. Such silane coupling agents have poor compatibility with water or hydrophilic polymerizable monomers contained in dental adhesives, dental primers, or other such dental compositions for the purpose of improving adhesive properties to tooth structure. Presumably, this increases the probability of the silane coupling agents contacting one another in the system, if not undergoing phase separation. A probable result is an increased likelihood of self-condensation reaction between the silane coupling agents, and increased viscosity or thixotropy, causing a considerable property change during storage. In contrast, an organosilicon compound (A) of the present invention has relatively high hydrophilicity due to the presence of an oxygen atom, such as that in an ether bond, in X of the spacers X and Y This probably explains the increased compatibility of organosilicon compound (A) with water or hydrophilic polymerizable monomers compared to silane coupling agents that have been used for conventional dental compositions. The organosilicon compound (A) is therefore less likely to contact with each other in the system, and there is a reduced likelihood of self-condensation reaction between silane coupling agents (organosilicon compound (A)), reducing the property change during storage.

Organosilicon Compound (A)

An organosilicon compound (A) of the present invention is represented by the following general formula (1), $$Z—X_m—Y—SiR^1{}_nR^2{}_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$, $R^2$, and X each may be the same or different when $R^1$, $R^2$, or X is plural.

Z represents a (meth)acryloyloxy group, a (meth)acrylamide group, a mercapto group, or an epoxy group. For considerations such as further improvement of adhesive properties to both dental restoration materials and tooth structure, Z is preferably a (meth)acryloyloxy group or a (meth)acrylamide group, more preferably a (meth)acryloyloxy group.

Y represents a divalent hydrocarbon group having 1 to 30 carbon atoms. For considerations such as stable properties, the divalent hydrocarbon group is preferably one with 1 to 20 carbon atoms, more preferably one with 1 to 15 carbon atoms, even more preferably one with 1 to 10 carbon atoms, particularly preferably one with 1 to 5 carbon atoms. The divalent hydrocarbon group may be optionally substituted. Examples of the substituent include a linear or branched alkyl group having 1 to 6 carbon atoms, and a halogen atom. The number of substituents is not particularly limited, and may be 1 to 10, 1 to 6, or 1 to 3. A certain embodiment may be, for example, an organosilicon compound (A) in which Y is an unsubstituted divalent hydrocarbon group.

X represents a divalent organic group with a ratio C/O of 1 to 3, where C is the total number of carbon atoms, and O is the total number of oxygen atoms. As noted above, an organosilicon compound (A) of the present invention has relatively high hydrophilicity due to the presence of an oxygen atom, such as that in an ether bond, in the spacer X, and is highly compatible with water and hydrophilic polymerizable monomers. The divalent organic group represented by X is not particularly limited, as long as it contains an oxygen atom such as that in an ether bond, and the ratio C/O of the total number of carbon atoms and the total number of oxygen atoms is 1 to 3. It is, however, preferable that the divalent organic group contain an ether bond in the backbone. For considerations such as providing an improved balance between property stability and adhesive properties in the dental composition, C/O is preferably 1 or 2. For considerations such as providing more stable properties in the dental composition, the number of carbon atoms in X is preferably 1 to 3.

Preferably, X is a group represented by the following formula (2), (3), or (4). Preferred is formula (3) for considerations such as providing an improved balance between property stability and adhesive properties in the dental composition.

$$—CH_2O— \quad (2)$$

$$—CH_2CH_2O— \quad (3)$$

$$—CH_2CH_2CH_2O— \quad (4)$$

The symbol m represents an integer of 1 to 8. For considerations such as stabilizing the properties of the dental composition, m is preferably an integer of 1 to 4, more preferably 1 or 2. X may be the same or different when X is plural.

Examples of the divalent hydrocarbon group represented by Y include an alkenylene group and an alkylene group. Preferred is an alkylene group. The alkenylene group having 2 to 30 carbon atoms may be linear or branched. Examples include a vinylene group, a propenylene group, a butenylene group, a pentenylene group, a hexenylene group, an octenylene group, a nonenylene group, and a decenylene group. The alkylene group having 1 to 30 carbon atoms may be linear or branched. Examples include a methylene group, an ethylene group, an n-propylene group, an isopropylene group, an n-butylene group, and an n-pentylene group. Preferred are an ethylene group and an n-propylene group. More preferred is an ethylene group.

The alkyl group represented by $R^1$ is not particularly limited, and may be, for example, an alkyl group having 1 to 5 carbon atoms. More specific examples include a methyl group, an ethyl group, an n-propyl group, an isopropyl group, an n-butyl group, and an n-pentyl group.

The aryl group represented by $R^1$ is not particularly limited, and may be, for example, an aryl group having 6 to 10 carbon atoms. More specific examples include a phenyl group and a naphthyl group.

The aralkyl group represented by $R^1$ is not particularly limited, and may be, for example, an aralkyl group having 7 to 12 carbon atoms. More specific examples include a benzyl group.

For considerations such as further improvement of adhesive properties to dental restoration materials, $R^1$ is preferably an alkyl group, more preferably an alkyl group having 1 to 5 carbon atoms, even more preferably a methyl group.

The hydrolyzable group represented by $R^2$ may be a group that can undergo hydrolysis to form a silanol group with the silicon atom attached to it. Examples include an alkoxy group, an acyloxy group, a siloxy group, and a halogen atom.

The alkoxy group is not particularly limited, and may be linear or branched. Examples include an alkoxy group having 1 to 5 carbon atoms. More specific examples include a methoxy group, an ethoxy group, an n-propoxy group, an isopropoxy group, an n-butoxy group, and an n-pentyloxy group.

The acyloxy group is not particularly limited, and may be linear or branched. Examples include an acyloxy group having 1 to 5 carbon atoms. More specific examples include a formyloxy group, an acetoxy group, an n-propionyloxy group, an isopropionyloxy group, an n-butanoyloxy group, and an n-pentanoyloxy group.

The siloxy group is not particularly limited, and may be, for example, a trimethylsiloxy group.

The halogen atom is not particularly limited, and may be, for example, a fluorine atom, a chlorine atom, a bromine atom, or an iodine atom.

For considerations such as further improvement of adhesive properties to dental restoration materials, $R^2$ is preferably an alkoxy group, more preferably an alkoxy group having 1 to 5 carbon atoms, even more preferably a methoxy group or an ethoxy group.

The symbol n represents 0, 1, or 2. Preferably, n is 1 or 2 because it discourages the self-condensation reaction of organosilicon compound (A), or reduces the steric hindrance in the condensate of organosilicon compound (A) to allow $R^2$ originally present in organosilicon compound (A) to more easily bind to a dental restoration material. When n is 0 or 1, the plurality of $R^2$ may be the same or different from each other. When n is 2, the plurality of $R^1$ may be the same or different from each other.

Specific examples of an organosilicon compound (A) of the present invention are as follows.

[Chem. 1]
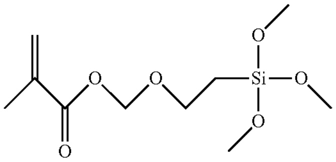
[Chem. 2]
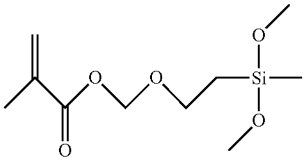
[Chem. 3]
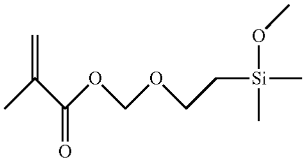
[Chem. 4]
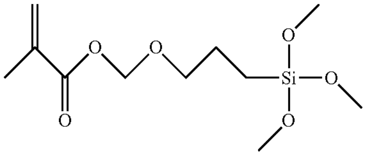
[Chem. 5]
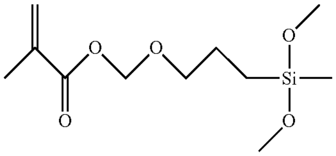
[Chem. 6]
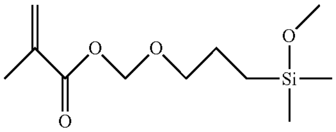
[Chem. 7]
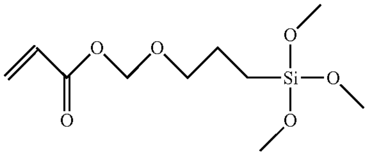
[Chem. 8]
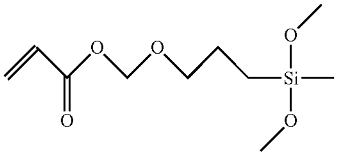
[Chem. 9]
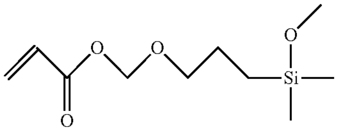
-continued
[Chem. 10]
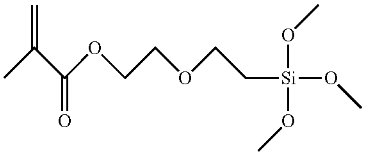
[Chem. 11]
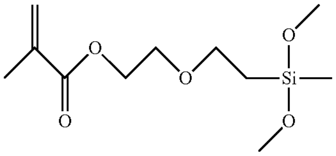
[Chem. 12]
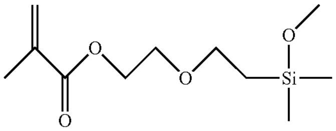
[Chem. 13]
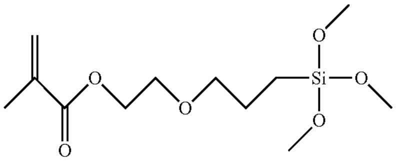
[Chem. 14]
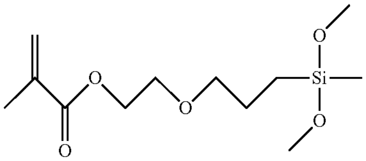
[Chem. 15]
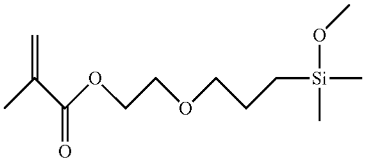
[Chem. 16]
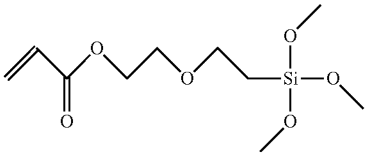
[Chem. 17]
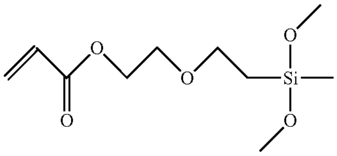
[Chem. 18]
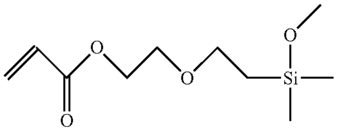

-continued
[Chem. 19]
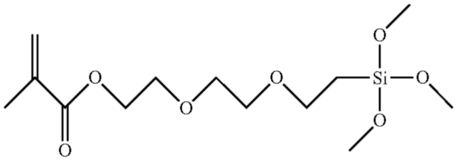
[Chem. 20]
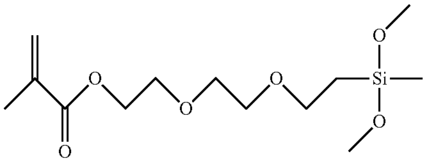
[Chem. 21]
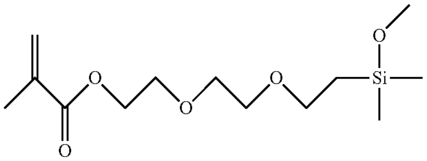
[Chem. 22]
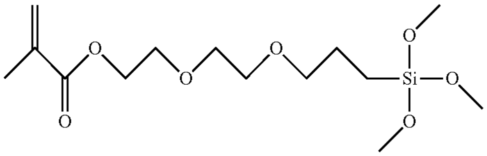
[Chem. 23]
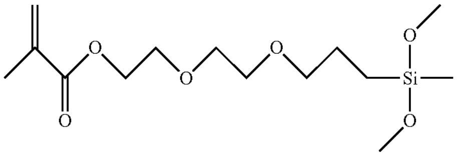
[Chem. 24]
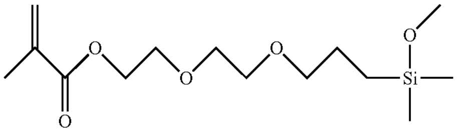
[Chem. 25]
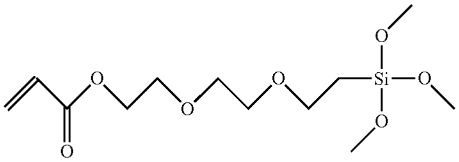
[Chem. 26]
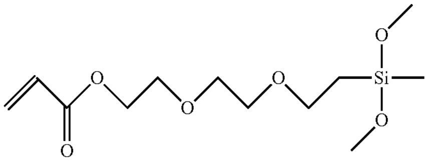
-continued
[Chem. 27]
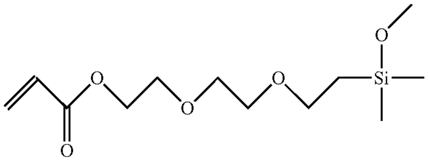
[Chem. 28]
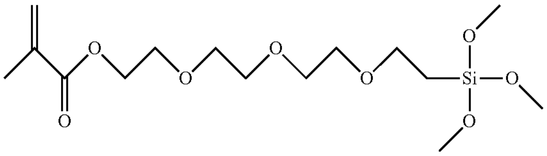
[Chem. 29]
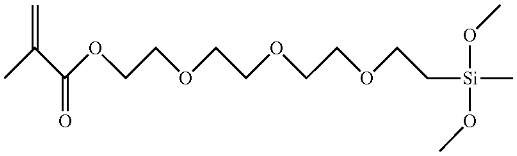
[Chem. 30]
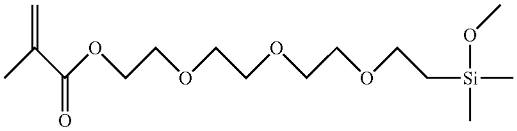
[Chem. 31]
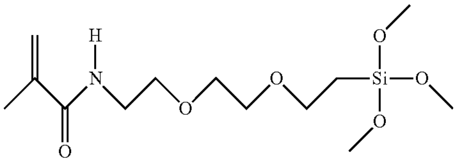
[Chem. 32]
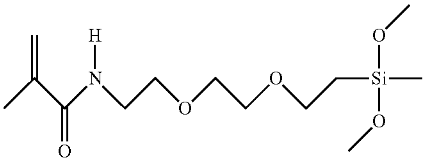
[Chem. 33]
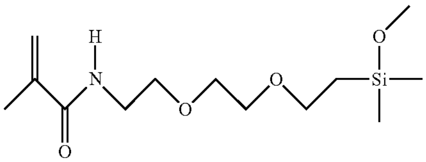
[Chem. 34]
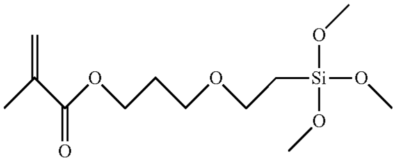

-continued

[Chem. 35]

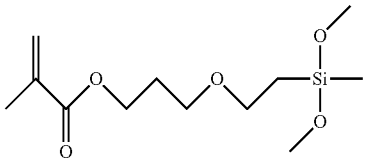

[Chem. 36]

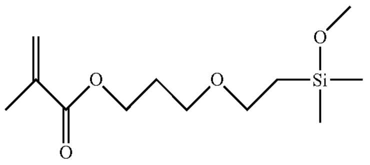

[Chem. 37]

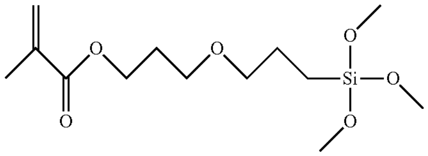

[Chem. 38]

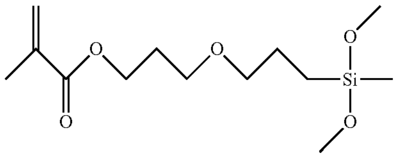

[Chem. 39]

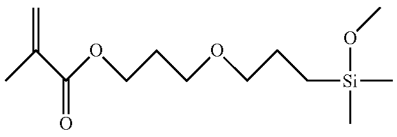

[Chem. 40]

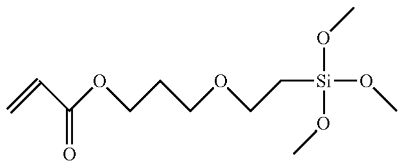

[Chem. 41]

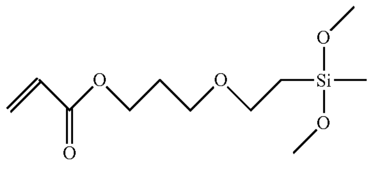

[Chem. 42]

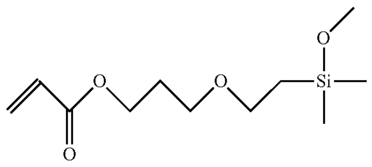

-continued

[Chem. 43]

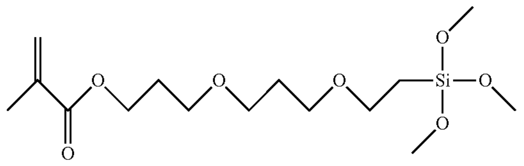

[Chem. 44]

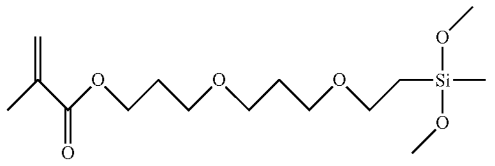

[Chem. 45]

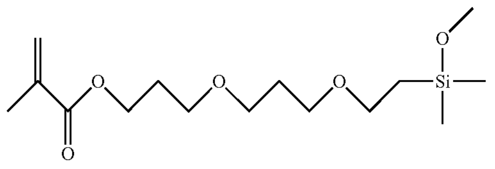

[Chem. 46]

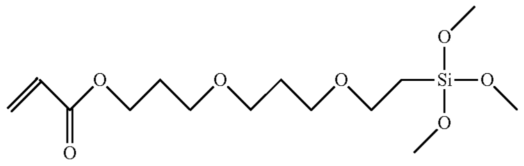

[Chem. 47]

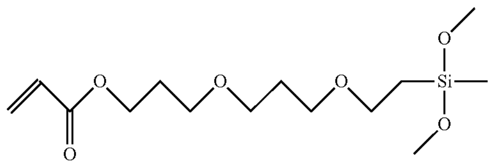

[Chem. 48]

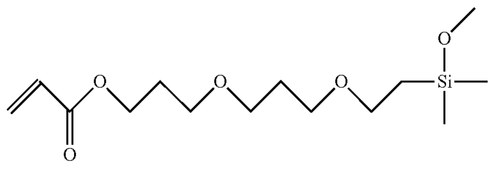

The organosilicon compound (A) may be a precursor that becomes an organosilicon compound represented by formula (1) after hydrolysis. The organosilicon compound (A) may be used alone, or two or more thereof may be used in combination.

For considerations such as further improvement of adhesive properties to both dental restoration materials and tooth structure, the content of the organosilicon compound (A) in a dental composition of the present invention is preferably 0.1 mass % or more, more preferably 1 mass % or more, even more preferably 3 mass % or more. The content of organosilicon compound (A) is preferably 50 mass % or less, more preferably 30 mass % or less, even more preferably 20 mass % or less, particularly preferably 15 mass % or less. The organosilicon compound (A) may undergo hydrolysis and/or condensation in the dental composition. In such cases, the content means the content of organosilicon compound (A) by assuming that no such hydrolysis and/or condensation have taken place.

Monomer (B) Having Acidic Group

Preferably, a dental composition of the present invention further comprises a monomer (B) having an acidic group. The monomer (B) having an acidic group can improve adhesive properties to tooth structure by binding to tooth structure through demineralization and penetration into tooth structure. The monomer (B) having an acidic group may be a monomer having at least one acidic group such as a phosphoric acid group, a phosphonic acid group, a pyrophosphoric acid group, a carboxylic acid group, and a sulfonic acid group, and at least one polymerizable group such as an acryloyl group, a methacryloyl group, an acrylamide group, and a methacrylamide group. In view of adhesive properties to enamel, the monomer (B) having an acidic group is preferably a monofunctional monomer having any one of an acryloyl group, a methacryloyl group, an acrylamide group, and a methacrylamide group. Specific examples are as follows.

Examples of the monomer having a phosphoric acid group include:

- phosphoric acid group-containing monofunctional (meth) acrylate compounds such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl)hydrogen phosphate, and 2-(meth)acryloyloxypropyl-(4-methoxyphenyl)hydrogen phosphate, and acid chlorides, alkali metal salts, and ammonium salts of these; and
- phosphoric acid group-containing bifunctional (meth) acrylate compounds such as bis[2-(meth)acryloyloxyethyl]hydrogen phosphate, bis[4-(meth)acryloyloxybutyl]hydrogen phosphate, bis[6-(meth) acryloyloxyhexyl]hydrogen phosphate, bis[8-(meth) acryloyloxyoctyl]hydrogen phosphate, bis[9-(meth) acryloyloxynonyl]hydrogen phosphate, bis[10-(meth) acryloyloxydecyl]hydrogen phosphate, and 1,3-di (meth)acryloyloxypropyl dihydrogen phosphate, and acid chlorides, alkali metal salts, and ammonium salts of these.

Examples of the monomer having a phosphonic acid group include 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth) acryloyloxyhexylphosphonoacetate, and 10-(meth)acryloyloxydecylphosphonoacetate, and acid chlorides, alkali metal salts, and ammonium salts of these.

Examples of the monomer having a pyrophosphoric acid group include bis[2-(meth)acryloyloxyethyl] pyrophosphate, bis[4-(meth)acryloyloxybutyl]pyrophosphate, bis[6-(meth)acryloyloxyhexyl] pyrophosphate, bis[8-(meth)acryloyloxyoctyl] pyrophosphate, and bis[10-(meth) acryloyloxydecyl]pyrophosphate, and acid chlorides, alkali metal salts, and ammonium salts of these.

Examples of the monomer having a carboxylic acid group include (meth)acrylic acid, 4-(meth)acryloyloxyethoxycarbonylphthalic acid, 4-(meth)acryloyloxyethyltrimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and 5-(meth)acryloylaminopentylcarboxylic acid, and acid anhydrides, acid chlorides, alkali metal salts, and ammonium salts of these.

Examples of the monomer having a sulfonic acid group include 2-(meth)acrylamide-2-methylpropanesulfonic acid, and 2-sulfoethyl (meth)acrylate, and acid chlorides, alkali metal salts, and ammonium salts of these.

In view of considerations such as the ability to exhibit more superior adhesive properties to tooth structure, the monomer (B) having an acidic group is preferably a monomer having a phosphoric acid group, or a monomer having a pyrophosphoric acid group, more preferably a monomer having a phosphoric acid group, even more preferably a monofunctional monomer having a phosphoric acid group. Preferred among these are (meth)acrylate monofunctional monomers having a phosphoric acid group with a C6 to C20 alkyl or alkylene group as a backbone within the molecule, more preferably (meth)acrylate monofunctional monomers having a phosphoric acid group with a C8 to C12 alkylene group as a backbone within the molecule, such as 10-methacryloyloxydecyl dihydrogen phosphate. The monomer (B) having an acidic group may be used alone, or two or more thereof may be used in combination.

For considerations such as further improvement of adhesive properties to both dental restoration materials and tooth structure, the content of the monomer (B) having an acidic group in a dental composition of the present invention is preferably 1 mass % or more, more preferably 2 mass % or more, even more preferably 3 mass % or more based on the mass of all monomers contained in the dental composition. The content of the monomer (B) having an acidic group is preferably 50 mass % or less, more preferably 30 mass % or less, even more preferably 20 mass % or less. In the present specification, typical examples of "all monomers contained in the dental composition" include radical polymerizable monomers, such as monomers having a (meth)acryloyl group contained in the dental composition, and all such monomers that do not classify as organosilicon compound (A).

Water (C)

Preferably, a dental composition of the present invention further comprises water (C). The presence of water (C) can promote the demineralizing effect of the monomer (B) having an acidic group. In view of avoiding inclusion of impurities that have adverse effect on adhesive properties, the water used for the preparation of a dental composition of the present invention is preferably distilled water or ion-exchange water.

In order to obtain a dental composition that exhibits high adhesive properties to dental restoration materials such as porcelain, as well as tooth structure, the content of water (C) in a dental composition of the present invention is preferably 1.0 mass % or more, more preferably 5.0 mass % or more, even more preferably 8.0 mass % or more. The content of water (C) is preferably 50 mass % or less, more preferably 30 mass % or less, even more preferably 20 mass % or less because the adhesive properties decrease when the content of water (C) is excessively high.

Monomer (D) Having No Acidic Group

In view of adhesive properties, it is preferable that a dental composition of the present invention further comprise a monomer (D) having no acidic group. The monomer (D) having no acidic group may be a known monomer having no acidic group. Examples include a hydrophobic monomer (D-1) having no acidic group, and a hydrophilic monomer (D-2) having no acidic group. The monomer (D) having no acidic group may be used alone, or two or more thereof may be used in combination. For example, the monomer (D) having no acidic group may be a combination of a hydrophobic monomer (D-1) having no acidic group and a hydrophilic monomer (D-2) having no acidic group.

(i) Hydrophobic Monomer (D-1) Having No Acidic Group

With a dental composition of the present invention comprising a hydrophobic monomer (D-1) having no acidic group, the cured product (the product of curing of the dental composition) can have improved properties, including mechanical strength, and ease of handling. The hydrophobic monomer (D-1) having no acidic group is preferably a radical polymerizable monomer having a polymerizable group, with no acidic group. For considerations such as ease of radical polymerization, the polymerizable group is preferably a (meth)acryloyl group or a (meth)acrylamide group. The hydrophobic monomer (D-1) having no acidic group may be one having a solubility in water of less than 10 mass % at 25° C. Examples include crosslinkable monomers such as monofunctional monomers, aromatic bifunctional monomers, aliphatic bifunctional monomers, and tri- and higher-functional monomers.

Examples of the monofunctional monomers include 4-hydroxybutyl (meth)acrylate, 6-hydroxyhexyl (meth)acrylate, 8-hydroxyoctyl (meth)acrylate, 10-hydroxydecyl (meth) acrylate, octafluoropentyl (meth)acrylate, m-phenoxybenzyl (meth)acrylate, biphenylmethyl (meth)acrylate, O-phenylphenolethyl (meth)acrylate, and O-phenyl(EO)2 (meth) acrylate.

Examples of the aromatic bifunctional monomers include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth) acryloyloxydiethoxyphenyl)-2-(4-(meth) acryloyloxyethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxypropoxyphenyl)propane, and 2,2-bis(4-(meth) acryloyloxyisopropoxyphenyl)propane.

Preferred among these are 2,2-bis[4-(3-methacryloyloxy-2-hydroxypropoxy)phenyl]propane (commonly known as "Bis-GMA"), 2,2-bis(4-(meth)acryloyloxyethoxyphenyl) propane, 2,2-bis(4-methacryloyloxypolyethoxyphenyl)propane (average number of moles of ethoxy group added: 2.6; commonly known as "D-2.6E"), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, and 2,2-bis(4-(meth) acryloyloxypentaethoxyphenyl)propane, more preferably 2,2-bis[4-(3-methacryloyloxy-2-hydroxypropoxy)phenyl] propane (Bis-GMA), and 2,2-bis(4-methacryloyloxypolyethoxyphenyl)propane (average number of moles of ethoxy group added: 2.6; commonly known as "D-2.6E").

Examples of the aliphatic bifunctional monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth) acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl)di(meth)acrylate, N-methacryloyloxyethylacrylamide, N-methacryloyloxypropylacrylamide, N-methacryloyloxybutylacrylamide, N-(1-ethyl-(2-methacryloyloxy)ethyl)acrylamide, and N-(2-(2-methacryloyloxyethoxy)ethyl)acrylamide.

Preferred among these are glycerol di(meth)acrylate, triethylene glycol diacrylate, triethylene glycol dimethacrylate (commonly known as "3G"), neopentyl glycol di(meth) acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl)dimethacrylate (commonly known as "UDMA"), N-methacryloyloxyethylacrylamide (commonly known as "MAEA"), and N-methacryloyloxypropylacrylamide.

Examples of the tri- and higher-functional monomers include trimethylolpropane tri(meth)acrylate, trimethylolethane tri(meth)acrylate, trimethylolmethane tri(meth)acrylate, pentaerythritol tri(meth)acrylate, pentaerythritol tetra (meth)acrylate, dipentaerythritol penta(meth)acrylate, N,N-(2,2,4-trimethylhexamethylene)bis[2-(aminocarboxy) propane-1,3-diol]tetra(meth)acrylate, and 1,7-diacryloyloxy-2,2,6,6-tetra(meth)acryloyloxymethyl-4-oxaheptane.

Preferred among these is N,N-(2,2,4-trimethylhexamethylene)bis[2-(aminocarboxy)propane-1,3-diol]tetrarmethacrylate.

In view of the mechanical strength and ease of handling of the cured product, the hydrophobic monomer (D-1) having no acidic group is preferably an aromatic bifunctional monomer, or an aliphatic bifunctional monomer. In view of adhesion, and the mechanical strength of the cured product, more preferred are Bis-GMA, D-2.6E, 3G, UDMA, and MAEA, and even more preferred are Bis-GMA, 3G, UDMA, and MAEA. The hydrophobic monomer (D-1) having no acidic group may be used alone, or two or more thereof may be used in combination.

In view of considerations such as the mechanical strength and ease of handling of the cured product (the product of curing of the dental composition), the content of the hydrophobic monomer (D-1) having no acidic group in a dental composition of the present invention is preferably 9 mass % or more, more preferably 15 mass % or more, even more preferably 20 mass % or more, particularly preferably 25 mass % or more based on the mass of all monomers contained in the dental composition. The content of the hydrophobic monomer (D-1) having no acidic group is preferably 90 mass % or less, more preferably 80 mass % or less, even more preferably 75 mass % or less, particularly preferably 70 mass % or less.

(ii) Hydrophilic Monomer (D-2) Having No Acidic Group

With a dental composition of the present invention comprising a hydrophilic monomer (D-2) having no acidic group, it is possible to more greatly inhibit the self-condensation reaction of the organosilicon compound (A) in the dental composition, and reduce the change in the properties of the dental composition during storage, in addition to improving adhesive properties to tooth structure. The hydrophilic monomer (D-2) having no acidic group is preferably a radical polymerizable monomer having a polymerizable group, with no acidic group. For considerations such as ease of radical polymerization, the polymerizable group is preferably a (meth)acryloyl group or a (meth)acrylamide group. The hydrophilic monomer (D-2) having no acidic group may be one having a solubility in water of 10 mass % or more at 25° C., preferably one with a solubility in water of 30 mass % or more at 25° C., even more preferably one that can dissolve in water in any proportions at 25° C.

The hydrophilic monomer (D-2) having no acidic group is preferably one having a hydrophilic group such as a hydroxyl group, an oxymethylene group, an oxyethylene group, an oxypropylene group, or an amide group. Examples include (meth)acrylates such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-trimethylammoniumethyl (meth)acryl chloride, and polyethylene glycol di(meth)acrylate (with nine or more oxyethylene groups); and monofunctional (meth)acrylamides such as N-methylol (meth)acrylamide, N-hydroxyethyl (meth)acrylamide, N-methoxymethyl (meth)acrylamide, N-ethoxymethyl (meth)acrylamide, diacetone(meth)acrylamide, 4-(meth)acryloylmorpholine, and disubstituted (meth)acrylamides represented by the following general formula (6).

[Chem. 49]

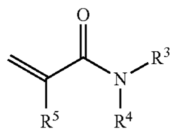

(6)

In the general formula (6), $R^3$ and $R^4$ are each independently an optionally substituted linear or branched alkyl group having 1 to 3 carbon atoms, and $R^5$ is a hydrogen atom or a methyl group.

Examples of the C1 to C3 alkyl groups represented by $R^3$ and $R^4$ include a methyl group, an ethyl group, an n-propyl group, and an isopropyl group. Examples of the optional substituents include a hydroxyl group.

Examples of the disubstituted (meth)acrylamides represented by the general formula (6) include N,N-dimethyl (meth)acrylamide, N,N-diethyl (meth)acrylamide, and N,N-di(hydroxyethyl)(meth)acrylamide. In view of considerations such as storage stability, preferred are N,N-dimethylacrylamide, and N,N-diethylacrylamide, more preferred is N,N-diethylacrylamide.

In view of adhesive properties to tooth structure, the hydrophilic monomer (D-2) having no acidic group is preferably 2-hydroxyethyl (meth)acrylate, 2,3-dihydroxypropyl (meth)acrylate, or a monofunctional (meth)acrylamide, more preferably 2-hydroxyethyl (meth)acrylate, 2,3-dihydroxypropyl (meth)acrylate, diacetone(meth)acrylamide, or a disubstituted (meth)acrylamide represented by the general formula (6), even more preferably 2-hydroxyethyl (meth) acrylate, or a disubstituted (meth)acrylamide represented by the general formula (6), particularly preferably 2-hydroxyethyl methacrylate, or N,N-diethylacrylamide. The hydrophilic monomer (D-2) having no acidic group may be used alone, or two or more thereof may be used in combination.

In view of considerations such as adhesive properties to tooth structure, and a reduction of property changes during storage, the content of the hydrophilic monomer (D-2) having no acidic group in a dental composition of the present invention is preferably 8 mass % or more, more preferably 10 mass % or more, even more preferably 12 mass % or more based on the mass of all monomers contained in the dental composition. The content of the hydrophilic monomer (D-2) having no acidic group is preferably 90 mass % or less, more preferably 80 mass % or less, even more preferably 70 mass % or less, particularly preferably 60 mass % or less.

For considerations such as further improvement of adhesive properties to both dental restoration materials and tooth structure, the total content of all monomers contained in a dental composition of the present invention, including the monomer (B) having an acidic group and the monomer (D) having no acidic group, is preferably 20 mass % or more, more preferably 35 mass % or more. The total content of all monomers is preferably 90 mass % or less, more preferably 80 mass % or less.

Polymerization Initiator (E)

In view of adhesive properties, it is preferable that a dental composition of the present invention further comprise a polymerization initiator (E). The polymerization initiator (E) may be a known polymerization initiator, and may be, for example, a photopolymerization initiator (E-1) or a chemical polymerization initiator (E-2). The polymerization initiator (E) may be used alone, or two or more thereof may be used in combination. For example, the polymerization initiator (E) may be a combination of a photopolymerization initiator (E-1) and a chemical polymerization initiator (E-2).

(i) Photopolymerization Initiator (E-1)

Examples of the photopolymerization initiator (E-1) include (bis)acylphosphine oxides (including salts), thioxanthones (including salts such as quaternary ammonium salts), ketals, α-diketones, coumarins, anthraquinones, benzoin alkyl ether compounds, and α-aminoketone compounds.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di(2,6-dimethylphenyl)phosphonate.

Examples of bisacylphosphine oxides in the (bis)acylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis (2,3,6-trimethylbenzoyl)-2,4,4-trimethylpentylphosphine oxide.

The acylphosphine oxides may be water-soluble acylphosphine oxides. Examples of the water-soluble acylphosphine oxides include those having ions, such as alkali metal ions, alkali earth metal ions, pyridinium ions, or ammonium ions, within the acylphosphine oxide molecule. The water-soluble acylphosphine oxides can be synthesized by using methods disclosed in, for example, European Patent Number 0009348, and JP S57-197289 A.

Specific examples of the water-soluble acylphosphine oxides include monomethyl acetyl phosphonate·sodium salt, monomethyl(1-oxopropyl)phosphonate·sodium salt, monomethyl benzoyl phosphonate·sodium salt, monomethyl (1-oxobutyl)phosphonate·sodium salt, monomethyl(2-methyl-1-oxopropyl)phosphonate·sodium salt, acetyl phosphonate·sodium salt, methyl 4-(hydroxymethoxyphosphinyl)-4-oxobutanoate·sodium salt, methyl 4-oxo-4-phosphonobutanoate·monosodium salt, acetylphenylphosphinate·sodium salt, (1-oxopropyl) pentylphosphinate·sodium salt, methyl 4-(hydroxypentylphosphinyl)-4-oxobutanoate·sodium salt, acetylpentylphosphinate·sodium salt, acetylethylphosphinate·sodium salt, methyl 4-(hydroxymethylphosphinyl)-4-oxobutanoate·lithium salt, 4-(hydroxymethylphosphinyl)-4-oxobutanoic acid·dilithium salt, acetylphosphinate·sodium salt, acetylmethylphosphinate oxime·sodium salt, acetylmethylphosphinate-O-benzyl oxime·sodium salt, acetylmethylphosphinate semicarbazone·sodium salt, formylmethylphosphinate·sodium salt, methyl(1-oxopropyl) phosphinate·sodium salt, acetylmethylphosphinate thiosemicarbazone·sodium salt, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide.

Particularly preferred among these (bis)acylphosphine oxides are 2,4,6-trimethylbenzoyldiphenylphosphine oxide, 2,4,6-trimethylbenzoylmethoxyphenylphosphine oxide, bis (2,4,6-trimethylbenzoyl)phenylphosphine oxide, and sodium salts of 2,4,6-trimethylbenzoylphenylphosphine oxide.

Examples of the thioxanthones include thioxanthone, 2-chlorothioxanthen-9-one, 2-hydroxy-3-(9-oxy-9H-thioxanthen-4-yloxy)-N,N,N-trimethylpropaneaminium chloride, 2-hydroxy-3-(1-methyl-9-oxo-9H-thioxanthen-4-yloxy)-N,N,N-trimethyl-1-propaneaminium chloride, 2-hydroxy-3-(9-oxo-9H-thioxanthen-2-yloxy)-N,N,N-trimethyl-1-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Preferred among these thioxanthones are 2-chlorothioxanthen-9-one, and 2-hydroxy-3-(3,4-dimethyl-9H-thioxanthen-2-yloxy)-N,N,N-trimethyl-1-propaneaminium chloride.

Examples of the ketals include benzyl dimethyl ketal, and benzyl diethyl ketal.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Particularly preferred is camphorquinone for its maximum absorption wavelength occurring in the visible light region.

Examples of the coumarins include 3,3'-carbonylbis(7-diethylaminocoumarin), 3-(4-methoxybenzoyl)coumarin, 3-thienylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f] coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f] coumarin, 3-benzoyl-6-nitrocoumarin, 3-benzoyl-7-diethylaminocoumarin, 7-dimethylamino-3-(4-methoxybenzoyl) coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f] coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazolyl)-7-(diethylamino)coumarin, 3-(2-benzothiazolyl)-7-(dibutylamino)coumarin, 3-(2-benzoimidazolyl)-7-(diethylamino)coumarin, 3-(2-benzothiazolyl)-7-(dioctylamino) coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrrano[6,7,8-ij]quinolizin-11-one, and 10-(2-benzothiazolyl)-2,3,6,7-tetrahydro-1,1,7,7-tetramethyl-1H,5H,11H-[1] benzopyrrano[6,7,8-ij]quinolizin-11-one.

Preferred among these coumarins are 3,3'-carbonylbis(7-diethylaminocoumarin), and 3,3'-carbonylbis(7-dibutylaminocoumarin).

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ether compounds include benzoin methyl ether, benzoin ethyl ether, benzoin isopropyl ether, and benzoin isobutyl ether.

Examples of the α-aminoketone compounds include 2-methyl-1-[4-(methylthio)phenyl]-2-morpholinopropan-1-one.

Preferred among these photopolymerization initiators (E-1) is at least one selected from the group consisting of a (bis)acylphosphine oxide, an α-diketone, and a coumarin. In this way, a dental composition can be obtained that has excellent photocurability both in the visible light region and the near ultraviolet region, and that shows sufficient photocurability regardless of whether the light source used is a halogen lamp, a light emitting diode (LED), or a xenon lamp.

(ii) Chemical Polymerization Initiator (E-2)

The chemical polymerization initiator (E-2) may be a known chemical polymerization initiator, particularly preferably an organic peroxide. Examples of the organic peroxide include ketone peroxides, hydroperoxides, diacyl peroxides, dialkyl peroxides, peroxyketals, peroxyesters, and peroxydicarbonates.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxy-isopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valeric acid ester.

Examples of the peroxyesters include α-cumyl peroxyneodecanoate, t-butyl peroxyneodecanoate, t-butyl peroxypivalate, 2,2,4-trimethylpentylperoxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvaleric acid.

Examples of the peroxydicarbonates include di-3-methoxybutylperoxydicarbonate, di(2-ethylhexyl)peroxydicarbonate, bis(4-t-butylcyclohexyl)peroxydicarbonate, diisopropylperoxydicarbonate, di-n-propylperoxydicarbonate, di(2-ethoxyethyl) peroxydicarbonate, and diallylperoxydicarbonate.

From an overall balance between safety, preservation stability, and radical generating potential, preferred among these organic peroxides are diacyl peroxides, particularly preferably benzoyl peroxide.

The polymerization initiator (E) preferably comprises the photopolymerization initiator (E-1).

In view of adhesive properties and other properties of the dental composition obtained, the content of the polymerization initiator (E) in a dental composition of the present invention is preferably 0.01 mass % or more, more preferably 0.05 mass % or more, even more preferably 0.1 mass % or more, most preferably 0.3 mass % or more. The content of polymerization initiator (E) is preferably 10 mass % or less.

Polymerization Accelerator (F)

A dental composition of the present invention may additionally comprise a polymerization accelerator (F). Preferably, the polymerization accelerator (F) is used with the polymerization initiator (E). The polymerization accelerator (F) may be a known polymerization accelerator. Examples include amines, sulfinic acids (including salts), borate compounds, derivatives of barbituric acid, triazine compounds, copper compounds, tin compounds, vanadium compounds, halogen compounds, aldehydes, thiol compounds, sulfites, bisulfites, and thiourea compounds. The polymerization accelerator (F) may be used alone, or two or more thereof may be used in combination.

The amines can be classified into aliphatic amines and aromatic amines. Examples of the aliphatic amines include aliphatic primary amines such as n-butylamine, n-hexylamine, and n-octylamine; aliphatic secondary amines such as diisopropylamine, dibutylamine, and N-methylethanolamine; and aliphatic tertiary amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. In view of the adhesive properties and preservation stability of the dental composition, preferred are tertiary aliphatic amines, more preferably N-methyldiethanolamine and triethanolamine.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N, N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino) benzoate, propyl 4-(N,N-dimethylamino)benzoate, n-butoxyethyl 4-(N,N-dimethylamino)benzoate, 2-[(meth) acryloyloxy]ethyl 4-(N,N-dimethylamino)benzoate, 4-(N, N-dimethylamino)benzophenone, butyl 4-dimethylaminobenzoate, and 4-(dimethylamino)benzonitrile. In view of the ability to impart superior adhesive properties to the dental composition, preferred are N,N-di(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone.

Examples of the sulfinic acids include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred are sodium benzenesulfinate, sodium p-toluenesulfininate, and sodium 2,4,6-triisopropylbenzenesulfinate.

The borate compounds are preferably arylborate compounds. Examples of the arylborate compounds include borate compounds having 1 to 4 aryl groups per molecule.

Examples of the borate compounds having one aryl group per molecule include trialkylphenylboron, trialkyl(p-chlorophenyl)boron, trialkyl(p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl (p-butyloxyphenyl)boron, trialkyl(m-butyloxyphenyl) boron, trialkyl(p-octyloxyphenyl)boron, trialkyl(m-octyloxyphenyl)boron (the alkyl groups in these examples are, for example, n-butyl, n-octyl, or n-dodecyl), and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having two aryl groups per molecule include dialkyl diphenylboron, dialkyl di(p-chlorophenyl)boron, dialkyl di(p-fluorophenyl)boron, dialkyl di[3,5-bis(trifluoromethyl)phenyl]boron, dialkyl di[3,5-bis(1,1,1,3,3,3-hexafluoro-2-methoxy-2-propyl)phenyl]boron, dialkyl di(p-nitrophenyl)boron, dialkyl di(m-nitrophenyl)boron, dialkyl di(p-butylphenyl)boron, dialkyl di(m-butylphenyl)boron, dialkyl di(p-butyloxyphenyl)boron, dialkyl di(m-butyloxyphenyl)boron, dialkyl di(p-octyloxyphenyl)boron, dialkyl di(m-octyloxyphenyl)boron (the alkyl groups in these examples are, for example, n-butyl, n-octyl, or n-dodecyl), and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having three aryl groups per molecule include monoalkyl triphenylboron, monoalkyl tri(p-chlorophenyl)boron, monoalkyl tri(p-fluorophenyl)boron, monoalkyl tri[3,5-bis(trifluoromethyl)phenyl]boron, monoalkyl tri[3,5-bis(1,1,1,3,3,3-hexafluoro-2-methoxy-2-propyl)phenyl]boron, monoalkyl tri(p-nitrophenyl)boron, monoalkyl tri(m-nitrophenyl)boron, monoalkyl tri(p-butylphenyl)boron, monoalkyl tri(m-butylphenyl)boron, monoalkyl tri(p-butyloxyphenyl)boron, monoalkyl tri(m-butyloxyphenyl)boron, monoalkyl tri(p-octyloxyphenyl)boron, monoalkyl tri(m-octyloxyphenyl) boron (the alkyl groups in these examples are, for example, n-butyl, n-octyl, or n-dodecyl), and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having four aryl groups per molecule include tetraphenylboron, tetrakis(p-chlorophenyl)boron, tetrakis(p-fluorophenyl)boron, tetrakis [3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, (p-octyloxyphenyl)triphenylboron, and salts of these (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

In view of preservation stability, preferred among these arylborate compounds are borate compounds having three or four aryl groups per molecule. The arylborate compounds may be used alone, or two or more thereof may be used in combination.

Examples of the derivatives of barbituric acid include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, thiobarbituric acid, and salts of these. Example salts of the derivatives of barbituric acid include alkali metal salts, and alkali-earth metal salts. More specific examples include sodium 5-butylbarbiturate, sodium 1,3,5-trimethylbarbiturate, and sodium 1-cyclohexyl-5-ethylbarbiturate.

Particularly preferred as derivatives of barbituric acid are, for example, 5-butylbarbituric acid, 1,3,5-trimethylbarbituric acid, 1-cyclohexyl-5-ethylbarbituric acid, 1-benzyl-5-phenylbarbituric acid, and sodium salts of these.

Examples of the triazine compounds include 2,4,6-tris (trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis (trichloromethyl)-s-triazine, 2-(2,4-dichlorophenyl)-4,6-bis (trichloromethyl)-s-triazine, 2-(p-bromophenyl)-4,6-bis (trichloromethyl)-s-triazine, 2-(p-tolyl)-4,6-bis (trichloromethyl)-s-triazine, 2-n-propyl-4,6-bis (trichloromethyl)-s-triazine 2-(α,α,β-trichloroethyl)-4,6-bis (trichloromethyl)-s-triazine, 2-styryl-4,6-bis (trichloromethyl)-s-triazine, 2-[2-(p-methoxyphenyl) ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis (trichloromethyl)-s-triazine, 2-[2-(3,4-dimethoxyphenyl) ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis (trichloromethyl)-s-triazine, and 2-[2-{N,N-diallylamino}ethoxy]-4,6-bis(trichloromethyl)-s-triazine.

In view of polymerization activity, preferred among these triazine compounds is 2,4,6-tris(trichloromethyl)-s-triazine. In view of preservation stability, preferred are 2-phenyl-4,6-bis(trichloromethyl)-s-triazine, 2-(p-chlorophenyl)-4,6-bis(trichloromethyl)-s-triazine, and 2-(4-biphenylyl)-4,6-bis (trichloromethyl)-s-triazine. The triazine compounds may be used alone, or two or more thereof may be used in combination.

Preferred for use as copper compounds are, for example, copper acetylacetonate, copper(II) acetate, copper oleate, copper(II) chloride, and copper(II) bromide.

Examples of the tin compounds include di-n-butyltin dimaleate, di-n-octyltin dimaleate, di-n-octyltin dilaurate, and di-n-butyltin dilaurate. Preferred are di-n-octyltin dilaurate and di-n-butyltin dilaurate.

The vanadium compounds are preferably vanadium compounds with a valency of IV or V. Examples of vanadium compounds with a valency of IV or V include vanadium(IV) oxide, vanadium(IV)oxy acetylacetonate, vanadyl oxalate, vanadyl sulfate, vanadium(IV) oxobis(1-phenyl-1,3-butanedionate), bis(maltolato)oxovanadium(IV), vanadium(V) oxide, sodium metavanadate, and ammonium metavanadate.

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde, and derivatives of benzaldehyde. Examples of derivatives of benzaldehyde include dimethylaminobenzaldehyde, p-methoxybenzaldehyde, p-ethoxybenzaldehyde, and p-n-octyloxybenzaldehyde. In view of adhesive properties, preferred is p-n-octyloxybenzaldehyde.

Examples of the thiol compounds include 3-mercaptopropyltrimethoxysilane, 2-mercaptobenzoxazole, decanethiol, and thiobenzoic acid.

Examples of the sulfites include sodium sulfite, potassium sulfite, calcium sulfite, and ammonium sulfite.

Examples of the bisulfites include sodium bisulfite and potassium bisulfite.

Examples of the thiourea compounds include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

In view of adhesive properties and other properties of the dental composition obtained, the content of the polymerization accelerator (F) in a dental composition of the present invention is preferably 0.01 mass % or more, more preferably 0.05 mass % or more, even more preferably 0.1 mass % or more. The content of polymerization accelerator (F) is preferably 10 mass % or less, more preferably 7 mass % or less, even more preferably 5 mass % or less.

Organic Solvent (G)

For considerations such as the ability to more greatly improve adhesive properties, spreadability, and penetrability into tooth structure, and prevent separation of the components in the dental composition, it is preferable that a dental composition of the present invention additionally comprise an organic solvent (G).

Examples of the organic solvent (G) include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Considering both body's safety and ease of removal based on volatility, preferred are water-soluble organic solvents. Specifically, preferred are ethanol, 2-propanol, 2-methyl-2-propanol, acetone, and tetrahydrofuran. More preferred are ethanol, 2-propanol, 2-methyl-2-propanol, and tetrahydrofuran. The organic solvent (G) may be used alone, or two or more thereof may be used in combination.

The content of the organic solvent (G) in a dental composition of the present invention is preferably 1 mass % or more, more preferably 5 mass % or more, even more preferably 8 mass % or more. The content of organic solvent (G) is preferably 70 mass % or less, more preferably 50 mass % or less, even more preferably 30 mass % or less. In some embodiments, the organic solvent (G) may be absent.

Filler (H)

Preferably, a dental composition of the present invention further comprises a filler (H). The filler (H) can be classified into organic fillers, inorganic fillers, and organic-inorganic composite fillers. The filler (H) may be used alone, or two or more thereof may be used in combination. When two or more fillers are used in combination, the filler (H) may be, for example, a combination of fillers of different materials having different particle size distributions and different forms. The filler (H) may be a commercially available product.

Examples of the material of the organic fillers include polymethyl methacrylate, polyethyl methacrylate, a methyl methacrylate-ethyl methacrylate copolymer, crosslinked polymethyl methacrylate, crosslinked polyethyl methacrylate, polyamides, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. The organic filler may be used alone or two or more thereof may be used in combination. The shape of the organic filler is not particularly limited.

Examples of the material of the inorganic fillers include quartz, silica, alumina, silica-titania, silica-titania-barium oxide, silica-zirconia, silica-alumina, lanthanum glass, borosilicate glass, soda glass, barium glass, strontium glass, glass-ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. The inorganic filler may be used alone, or two or more thereof may be used in combination.

The shape of the inorganic filler is not particularly limited. The inorganic filler may be, for example, an irregularly shaped filler, or a spherical filler. In view of improving the mechanical strength of the cured product, the inorganic filler is preferably a spherical filler. Here, the spherical filler may be a filler having an average uniformity of 0.6 or more as measured for round-shaped particles observed in a unit field of a scanning electron micrograph (SEM) of fillers by dividing the diameter of a particle perpendicular to its maximum diameter by the maximum diameter. When the inorganic filler is a spherical filler, the average particle diameter of the spherical filler is preferably 0.1 μm or more because it enables the mechanical strength of the cured product to be maintained without causing a decrease in the filling rate of the spherical filler in the dental composition. The average particle diameter of the spherical filler is preferably 5 μm or less because it provides a surface area sufficient to maintain the mechanical strength in the cured product.

In order to adjust the flowability of the dental composition, the inorganic filler may be used after an optional surface treatment with a known surface treatment agent such as a silane coupling agent. Examples of the surface treatment agent include silane coupling agents such as vinyltrimethoxysilane, vinyltriethoxysilane, vinyltrichlorosilane, vinyl tri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane. The surface treatment agent may be used alone, or two or more thereof may be used in combination.

The organic-inorganic composite filler may be a filler obtained by adding a monomer compound to the inorganic filler, polymerizing the mixture in paste form, and pulverizing the polymerized filler. The organic-inorganic composite filler may be, for example, a TMPT filler (a filler obtained by mixing trimethylolpropane methacrylate and a silica filler, and pulverizing the mixture after polymerization). The shape of the organic-inorganic composite filler is not particularly limited.

The particle diameter of filler (H) is not particularly limited, and the average particle diameter may be appropriately selected. In view of considerations such as the ease of handling of the dental composition and the mechanical strength of the cured product obtained, the average particle diameter of filler (H) is preferably 0.001 μm or more, and is preferably 50 μm or less, more preferably 10 μm or less. In the present specification, the average particle diameter of filler (H) means the average particle diameter of the primary particles of filler (H) (average primary particle diameter). When the inorganic filler is surface treated with a surface treatment agent, the average particle diameter of the inorganic filler means the average particle diameter before surface treatment.

The average particle diameter of filler (H) can be determined by a laser diffraction scattering method or by observing particles with an electron microscope. Specifically, a laser diffraction scattering method is more convenient for the measurement of particles of 0.1 μm or more, whereas electron microscopy is a more convenient method of particle size measurement for ultrafine particles of less than 0.1 μm. A laser diffraction scattering method can be used to determine whether the particle size is 0.1 μm or more.

As an example of a laser diffraction scattering method, the average particle diameter can be determined by measuring the particle size by volume, using, for example, a laser diffraction particle size distribution analyzer (for example, SALD-2300 manufactured by Shimadzu Corporation) with a 0.2% sodium hexametaphosphate aqueous solution used as dispersion medium.

For the measurement of average particle diameter by electron microscopy, for example, particles may be photographed with a scanning electron microscope (for example, Model S-4000 manufactured by Hitachi), and the size of particles (at least 200 particles) observed in a unit field of the captured image may be measured with image-analyzing particle-size-distribution measurement software (such as Mac-View manufactured by Mountech Co., Ltd.) to determine the average particle diameter. Here the particle diameter is determined as an arithmetic mean value of the maximum and minimum lengths of particles, and the average particle diameter is calculated from the number of particles and the particle diameter.

The content of the filler (H) in a dental composition of the present invention is preferably 0.1 mass % or more, more preferably 0.5 mass % or more, even more preferably 1.0 mass % or more. The content of filler (H) is preferably 30 mass % or less, more preferably 20 mass % or less, even more preferably 10 mass % or less.

Other Components

A dental composition of the present invention may comprise a known additive to such an extent that it does not diminish the effects of the present invention. Examples of such additives include pH adjusters, polymerization inhibitors, fluorine-ion releasing components, ultraviolet absorbers, thickeners, colorants, fluorescent agents, fragrances, and anti-microbial substances. The additives may be used alone, or two or more thereof may be used in combination.

Examples of the anti-microbial substances include cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, and triclosan.

Examples of the polymerization inhibitors include hydroquinone, hydroquinone monomethyl ether, dibutylhydroquinone, dibutylhydroquinone monomethyl ether, t-butylcatechol, 2-t-butyl-4,6-dimethylphenol, 2,6-di-t-butylphenol, and 3,5-di-t-butyl-4-hydroxytoluene. The content of the polymerization inhibitor in a dental composition of the present invention is preferably 0.001 to 3.0 parts by mass.

The method of preparation of a dental composition of the present invention is not particularly limited, and a dental composition of the present invention can be obtained by mixing the components. The dental composition obtained may be provided as a one-pack type dental composition by being filled into a single container, for example.

A dental composition of the present invention exhibits high adhesive properties not only to tooth structure but also to dental restoration materials made of materials such as metal, composite resin, or porcelain. This makes a dental composition of the present invention suitable for use as a dental cement, a dental adhesive, or a dental primer, particularly a dental adhesive or dental primer, which is usually a hydrophilic system. Here, the dental restoration material may be one that has fractured in the oral cavity. The method of use of a dental composition of the present invention is not limited to specific methods, and a dental composition of the present invention can be used following an ordinary method.

When used for bonding of dental restoration materials, a dental composition of the present invention may be used with a primer such as a commercially available metal bonding primer, or with a dental surface cleaner such as hypochlorite or a hydrogen peroxide solution.

EXAMPLES

The present invention is described below in greater detail by way of EXAMPLES. However, the present invention is in no way limited by the following EXAMPLES. The following abbreviations are used in EXAMPLES.

[Organosilicon Compound (A)]

a1

[Chem. 50]

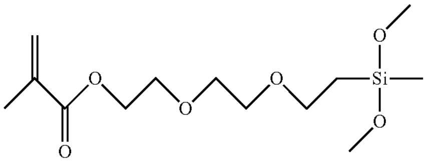

a2

[Chem. 51]

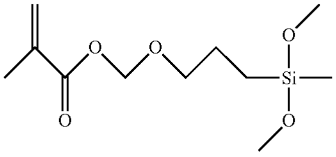

a3

[Chem. 52]

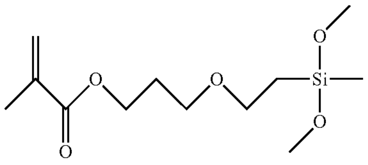

a4

[Chem. 53]

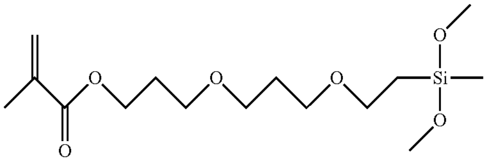

-continued a5

[Chem. 54]

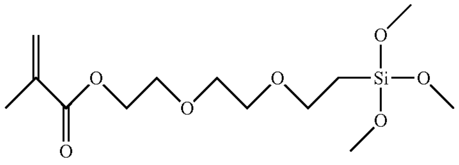

a6

[Chem. 55]

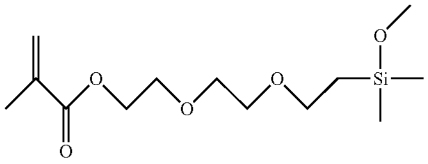

[Silane Coupling Agent that does not Classify as Organosilicon Compound (A)]

a'1

[Chem. 56]

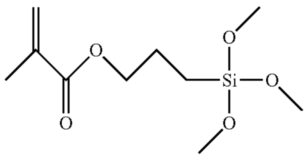

a'2

[Chem. 57]

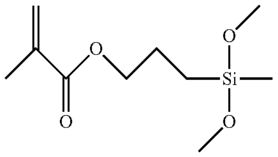

a'3

[Chem. 58]

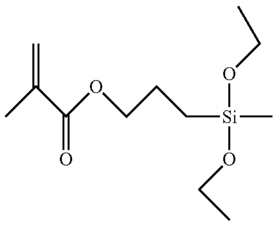

[Monomer (B) Having an Acidic Group]

MDP: 10-Methacryloyloxydecyl dihydrogen phosphate

[Hydrophobic Monomer (D-1) Having No Acidic Group]

Bis-GMA: 2,2-bis[4-(3-methacryloyloxy-2-hydroxypropoxy)phenyl]propane

MAEA: N-methacryloyloxyethylacrylamide

[Hydrophilic Monomer (D-2) Having No Acidic Group]

HEMA: 2-hydroxyethyl methacrylate

DEAA: N,N-diethylacrylamide

[Photopolymerization Initiator (E-1)]

CQ: camphorquinone

BAPO: bis(2,4,6-trimethylbenzoyl)phenylphosphine oxide

[Polymerization Accelerator (F)]

DABE: ethyl 4-(N,N-dimethylamino)benzoate

DEPT N,N-di(2-hydroxyethyl)-p-toluidine

[Solvent (G)]

EtOH: ethanol

[Filler (H)]

R972: particulate silica Aerosil® R 972 manufactured by Nippon Aerosil Co., Ltd.; average particle diameter: 16 nm

[Other Components]

BHT 3,5-di-t-butyl-4-hydroxytoluene (polymerization inhibitor)

Examples 1 to 14 and Comparative Examples 1 to 3

One-pack type dental compositions were prepared by mixing the components in the proportions shown in Tables 1 and 2. The dental compositions were then measured for viscosity, and tensile bond strength against dental porcelain and dentin, following the methods described below. Here, the dental compositions were also evaluated with respect to their thixotropy. The results are presented in Tables 1 and 2. For the evaluation of the preservation stability of the dental compositions, the dental compositions were measured immediately after preparation (as-prepared), and after being stored at 50° C. for 4 weeks (after 4-week storage at 50° C.).

Viscosity Measurement

The viscosity was measured for a 0.7 mL sample at 30° C. using a viscometer (viscometer TV-30E manufactured by Toki Sangyo Co., Ltd.; JIS K-7117-2:1999 compliant; a cone-plate type) with a 0.8°×R24 conical rotor). The measurement was started after 1 minute of preliminary heating (preheating), and the measured value after 3 minutes was determined as the viscosity value (n=2). The percentage viscosity increase (%) after 4-week storage at 50° C. was calculated by taking the viscosity immediately after preparation as 100%, using the following formula.

Percentage viscosity increase (%)={(viscosity after 4-week storage at 50° C.)−(viscosity immediately after preparation)}/(viscosity immediately after preparation)×100

Measurement of Tensile Bond Strength Against Dental Porcelain

A dental porcelain (feldspathic ceramic VITABLOCS® Mark II) was polished with #1000 silicon carbide paper (manufactured by Nihon Kenshi Co., Ltd.) under running water. After polishing, the surface was dried by removing water by air blowing. After drying, about a 150 μm-thick adhesive tape having a 5 mm circular hole was attached to the dried smooth surface to define a bonding area.

The dental composition prepared in each Example or Comparative Example was applied to the surface in the circular hole with a brush. After allowing the composition to stand for 3 seconds, the surface was dried by blowing air until the applied dental composition was no longer flowable. The dental composition was then cured by being exposed to light for 10 seconds, using a dental visible-light irradiator (PenCure 2000, manufactured by J. Morita Corp. under this trade name).

A dental filling composite resin (Clearfil® AP-X, manufactured by Kuraray Noritake Dental Inc. under this trade name) was applied to fill the surface of the cured dental composition, and the resin surface was covered with a release film (polyester). Thereafter, a glass slide was placed on the release film, and pressure was applied to flatten the surface of the applied dental filling composite resin. The dental filling composite resin was then cured by being exposed to light for 20 seconds through the release film using the dental visible-light irradiator.

A cylindrical stainless steel rod (7 mm in diameter, 2.5 cm in length) was then bonded at one end (circular cross section) to the surface of the cured dental filling composite resin, using a commercially available dental resin cement (Panavia® 21, manufactured by Kuraray Noritake Dental Inc. under this trade name). After bonding, the sample was left to stand at room temperature for 30 minutes, and was immersed in distilled water to obtain an adhesion test sample. A total of ten adhesion test samples were prepared, and these were allowed to stand for 24 hours in a thermostatic chamber maintained at 37° C. The samples were measured for tensile bond strength after being allowed to stand for 240 hours in a thermostatic chamber maintained at 70° C., under the following conditions.

For the measurement of tensile bond strength, the adhesion test samples were measured using a universal testing machine (Autograph AG-I 100 kN, manufactured by Shimadzu Corporation) with the crosshead speed set at 2 mm/min, and the mean value was calculated.

Measurement of Tensile Bond Strength Against Dentin

The labial surface of a bovine mandibular incisor was ground with #80 silicon carbide paper (manufactured by Nihon Kenshi Co., Ltd.) under running water to obtain a sample with an exposed, smooth dentin surface. The sample was then polished with #1000 silicon carbide paper (manufactured by Nihon Kenshi Co., Ltd.) under running water. The polished surface was dried by removing water by air blowing. After drying, about a 150 μm-thick adhesive tape having a 3 mm circular hole was attached to the dried smooth surface to define a bonding area.

The dental composition prepared in each Example or Comparative Example was applied to the surface in the circular hole with a brush. After allowing the composition to stand for 3 seconds, the surface was dried by blowing air until the applied dental composition was no longer flowable. The dental composition was then cured by being exposed to light for 10 seconds, using a dental visible-light irradiator (PenCure 2000, manufactured by J. Morita Corp. under this trade name).

A dental filling composite resin (Clearfil® AP-X, manufactured by Kuraray Noritake Dental Inc. under this trade name) was applied to fill the surface of the cured dental composition, and the resin surface was covered with a release film (polyester). Thereafter, a glass slide was placed on the release film, and pressure was applied to flatten the surface of the applied dental filling composite resin. The dental filling composite resin was then cured by being exposed to light for 20 seconds through the release film using the dental visible-light irradiator. A cylindrical stainless steel rod (7 mm in diameter, 2.5 cm in length) was then bonded at one end (circular cross section) to the surface of the cured dental filling composite resin, using a commercially available dental resin cement (Panavia® 21, manufactured by Kuraray Noritake Dental Inc. under this trade name). After bonding, the sample was left to stand at room temperature for 30 minutes, and was immersed in distilled water to obtain an adhesion test sample. A total of ten adhesion test samples were prepared, and these were allowed to stand for 24 hours in a thermostatic chamber maintained at 37° C. For the evaluation of bond durability, the tensile bond strength was measured under the conditions below, after 4,000 cycles of alternate immersion in 4° C. cold water and 60° C. hot water, 1 minute each.

For the measurement of tensile bond strength, the adhesion test samples were measured using a universal testing machine (Autograph AG-I 100 kN, manufactured by Shimadzu Corporation) with the crosshead speed set at 2 mm/min, and the mean value was calculated.

Evaluation of Thixotropy

Five milliliters of the dental composition prepared was filled into the bottle container of the Clearfil® Universal Bond Quick ER (manufactured by Kuraray Noritake Dental Inc.), and the container was stored at 50° C. for 4 weeks (n=3). The dental composition was evaluated as "Good" when it was easily able to fall out of the container in drops after storage, and "Poor" when any of the samples failed to drip out of the container, or when the samples were only able to drip in a limited fashion. When dripping the dental composition from the container, care was taken not to disturb or shake the composition more than necessary.

TABLE 1

| Components (mass %) | | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| Organosilicon compound (A) | a1 | 4.3 | 4.3 | 4.8 | 4.0 | | | | | |
| | a2 | | | | | 4.3 | | | | |
| | a3 | | | | | | 4.3 | | | |
| | a4 | | | | | | | 4.3 | | |
| | a5 | | | | | | | | 4.3 | |
| | a6 | | | | | | | | | 4.3 |
| Silane coupling agent other than | a'1 | | | | | | | | | |
| organosilicon compound (A) | a'2 | | | | | | | | | |
| | a'3 | | | | | | | | | |
| Monomer (B) having an acidic group | MDP | 8.5 | 8.5 | 9.5 | 8.0 | 8.5 | 8.5 | 8.5 | 8.5 | 8.5 |
| Water (C) | | 12.8 | 12.8 | 3.0 | 17.9 | 12.8 | 12.8 | 12.8 | 12.8 | 12.8 |
| Hydrophobic monomer (D-1) having no acidic group | Bis-GMA | 17.1 | 25.6 | 19.0 | 16.1 | 17.1 | 17.1 | 17.1 | 17.1 | 17.1 |
| | MAEA | 17.1 | 17.1 | 19.0 | 16.1 | 17.1 | 17.1 | 17.1 | 17.1 | 17.1 |
| Hydrophilic monomer (D-2) having no acidic group | HEMA | 8.5 | 17.1 | 9.5 | 8.0 | 8.5 | 8.5 | 8.5 | 8.5 | 8.5 |
| | DEAA | 8.5 | | 9.5 | 8.0 | 8.5 | 8.5 | 8.5 | 8.5 | 8.5 |
| Photopolymerization initiator (E-1) | CQ | 1.71 | 1.71 | 1.90 | 1.61 | 1.71 | 1.71 | 1.71 | 1.71 | 1.71 |
| | BAPO | 0.43 | 0.64 | 0.48 | 0.40 | 0.43 | 0.43 | 0.43 | 0.43 | 0.43 |
| Polymerization accelerator (F) | DABE | 1.71 | 0.85 | 1.90 | 1.61 | 1.71 | 1.71 | 1.71 | 1.71 | 1.71 |
| | DEPT | 0.43 | 0.64 | 0.48 | 0.40 | 0.43 | 0.43 | 0.43 | 0.43 | 0.43 |

TABLE 1-continued

| Components (mass %) | | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| Solvent (G) | EtOH | 12.8 | 12.8 | 14.3 | 12.1 | 12.8 | 12.8 | 12.8 | 12.8 | 12.8 |
| Filler (H) | R972 | 6.0 | 6.0 | 6.7 | 5.6 | 6.0 | 6.0 | 6.0 | 6.0 | 6.0 |
| Other components | BHT | 0.04 | 0.04 | 0.05 | 0.04 | 0.04 | 0.04 | 0.04 | 0.04 | 0.04 |
| Percentage viscosity increase (%) | | 18 | 14 | 5 | 29 | 18 | 13 | 21 | 28 | 15 |
| Tensile bond strength against dentin (MPa) | As-prepared | 18.6 | 18.7 | 15.4 | 18.1 | 18.6 | 18.7 | 18.2 | 18.2 | 18.0 |
| | After 4-week storage at 50° C. | 17.7 | 17.5 | 15.1 | 16.4 | 17.4 | 17.5 | 17.3 | 17.1 | 16.8 |
| Tensile bond strength against porcelain (MPa) | As-prepared | 18.1 | 17.8 | 18.4 | 17.0 | 17.2 | 17.6 | 16.7 | 14.6 | 17.9 |
| | After 4-week storage at 50° C. | 13.4 | 13.3 | 13.6 | 12.8 | 12.9 | 13.2 | 12.6 | 10.1 | 13.0 |
| Thixotropy | After 4-week storage at 50° C. | Good | Good | Good | Good | Good | Good | Good | Good | Good |

TABLE 2

| Components (mass %) | | Ex. 10 | Ex. 11 | Ex. 12 | Ex. 13 | Ex. 14 | Com. Ex. 1 | Com. Ex. 2 | Com. Ex. 3 |
|---|---|---|---|---|---|---|---|---|---|
| Organosilicon compound (A) | a1 | 2.6 | 5.9 | 4.3 | 4.3 | 4.4 | | | |
| | a2 | | | | | | | | |
| | a3 | | | | | | | | |
| | a4 | | | | | | | | |
| | a5 | | | | | | | | |
| | a6 | | | | | | | | |
| Silane coupling agent other than organosilicon compound (A) | a'1 | | | | | | | | 4.3 |
| | a'2 | | | | | | | 4.3 | |
| | a'3 | | | | | | 4.3 | | |
| Monomer (B) having an acidic group | MDP | 8.7 | 8.4 | 8.5 | 8.5 | 8.8 | 8.5 | 8.5 | 8.5 |
| Water (C) | | 13.0 | 12.6 | 12.8 | 12.8 | 10.5 | 12.8 | 12.8 | 12.8 |
| Hydrophobic monomer (D-1) having no acidic group | Bis-GMA | 17.4 | 16.8 | 25.6 | 17.1 | 17.5 | 17.1 | 17.1 | 17.1 |
| | MAEA | 17.4 | 16.8 | | 17.1 | 17.5 | 17.1 | 17.1 | 17.1 |
| Hydrophilic monomer (D-2) having no acidic group | HEMA | 8.7 | 8.4 | 17.1 | 8.5 | 17.5 | 8.5 | 8.5 | 17.1 |
| | DEAA | 8.7 | 8.4 | 8.5 | 8.5 | 13.2 | 8.5 | 8.5 | 8.5 |
| Photopolymerization initiator (E-1) | CQ | 1.74 | 1.68 | 1.71 | 2.14 | 1.75 | 1.71 | 1.71 | 1.71 |
| | BAPO | 0.43 | 0.42 | 0.43 | | 0.44 | 0.43 | 0.43 | 0.64 |
| Polymerization accelerator (F) | DABE | 1.74 | 1.68 | 1.71 | 2.14 | 1.75 | 1.71 | 1.71 | 0.85 |
| | DEPT | 0.43 | 0.42 | 0.43 | | 0.44 | 0.43 | 0.43 | 0.64 |
| Solvent (G) | EtOH | 13.0 | 12.6 | 12.8 | 12.8 | | 12.8 | 12.8 | 12.8 |
| Filler (H) | R972 | 6.1 | 5.9 | 6.0 | 6.0 | 6.1 | 6.0 | 6.0 | 6.0 |
| Other components | BHT | 0.04 | 0.04 | 0.04 | 0.04 | 0.04 | 0.04 | 0.04 | 0.04 |
| Percentage viscosity increase (%) | | 19 | 16 | 19 | 21 | 4 | 169 | 221 | 165 |
| Tensile bond strength against dentin (MPa) | As-prepared | 18.8 | 18.3 | 17.8 | 17.3 | 16.9 | 18.1 | 18.7 | 18.8 |
| | After 4-week storage at 50° C. | 17.8 | 17.5 | 16.6 | 16.4 | 16.0 | 17.0 | 17.6 | 17.8 |
| Tensile bond strength against porcelain (MPa) | As-prepared | 16.1 | 18.1 | 17.9 | 18.0 | 17.8 | 17.7 | 17.5 | 17.0 |
| | After 4-week storage at 50° C. | 12.1 | 14.0 | 13.2 | 13.1 | 13.0 | 9.9 | 9.4 | 4.3 |
| Thixotropy | After 4-week storage at 50° C. | Good | Good | Good | Good | Good | Poor | Poor | Poor |

As shown in Tables 1 and 2, the dental compositions according to the present invention (Examples 1 to 14) exhibited sufficient bond strength against dentin. The result of thixotropy evaluation was also desirable with a percentage viscosity increase of 30% or less. The bond strength against porcelain after 4-week storage at 50° C. was 10.0 MPa or more, suggesting that the self-condensation reaction of the silane coupling agent was reduced as a result of reduced contact between the molecules of organosilicon compound (A). In contrast, the dental compositions (Comparative Examples 1 to 3) that did not contain the organosilicon compound (A) but used a silane coupling agent that does not classify as organosilicon compound (A) had a percentage viscosity increase of 165% or more, and showed poor thixotropy in its evaluation because of the viscosity increase after 4-week storage at 50° C. The bond strength against porcelain after 4-week storage at 50° C. was 10.0 MPa or less, suggesting that the silane coupling agent has undergone a self-condensation reaction. As demonstrated above, the dental compositions according to the present invention showed superior effects compared to Comparative Examples 1 and 2, which correspond to Patent Literature 3, and Comparative Example 3, which used a traditionally common silane coupling agent.

The invention claimed is:

1. A dental composition comprising an organosilicon compound (A) represented by the following general formula (1), $$Z—X_m—Y—SiR^1_nR^2_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$, $R^2$, and X each may be the same or different when $R^1$, $R^2$, or X is plural.

2. The dental composition according to claim 1, wherein the number of carbon atoms in X is 1 to 3.

3. The dental composition according to claim 1, wherein X is a group represented by the following formula (2), (3), or (4), $$—H_2O— \quad (2)$$

$$—CH_2CH_2O— \quad (3)$$

$$—CH_2CH_2CH_2O— \quad (4).$$

4. The dental composition according to claim 1, wherein m is an integer of 1 to 4.

5. The dental composition according to claim 1, wherein n is 1 or 2.

6. The dental composition according to claim 1, wherein Z is a (meth)acryloyloxy group.

7. The dental composition according to claim 1, wherein R2 is an alkoxy group having 1 to 5 carbon atoms.

8. The dental composition according to claim 1, wherein the content of the organosilicon compound (A) is 0.1 to 50 mass %.

9. The dental composition according to claim 1, which further comprises a monomer (B) having an acidic group.

10. The dental composition according to claim 9, wherein the monomer (B) having an acidic group comprises a monomer having a phosphoric acid group.

11. The dental composition according to claim 1, which further comprises water (C).

12. The dental composition according to claim 1, which further comprises a monomer (D) having no acidic group.

13. The dental composition according to claim 12, wherein the monomer (D) having no acidic group comprises a hydrophilic monomer (D-2) having no acidic group.

14. The dental composition according to claim 13, which comprises 8 to 90 mass % of the hydrophilic monomer (D-2) having no acidic group based on the mass of all monomers contained in the dental composition.

15. A dental adhesive comprising the dental composition of claim 1.

16. An organosilicon compound (A) represented by the following general formula (1), $$Z—X_m—Y—SiR^1_nR^2_{(3-n)} \quad (1)$$

wherein Z represents a (meth)acryloyloxy group, a (meth) acrylamide group, a mercapto group, or an epoxy group, X represents a divalent organic group with a ratio C/O of 1 to 3, where C is the total number of carbon atoms, and O is the total number of oxygen atoms, Y represents a divalent hydrocarbon group having 1 to 30 carbon atoms, $R^1$ represents a group selected from the group consisting of an alkyl group, an aryl group, and an aralkyl group, $R^2$ represents a hydroxyl group or a hydrolyzable group, m represents an integer of 1 to 8, and n represents 0, 1, or 2, and wherein $R^1$, $R^2$, and X each may be the same or different when $R^1$, $R^2$, or X is plural.

17. The organosilicon compound (A) according to claim 16, wherein the number of carbon atoms in X is 1 to 3.

18. The organosilicon compound (A) according to claim 16, wherein X is a group represented by the following formula (2), (3), or (4), $$—CH_2O— \quad (2)$$

$$—CH_2CH_2O— \quad (3)$$

$$—CH_2CH_2CH_2O— \quad (4).$$

* * * * *